United States Patent
Desrochers

(10) Patent No.: US 8,986,293 B2
(45) Date of Patent: Mar. 24, 2015

(54) CRYOBALLOON REFRIGERANT DISPERSION CONTROL

(75) Inventor: Gilles Desrochers, Beaconsfield (CA)

(73) Assignee: Medtronic Cryocath LP, Toronto, Ontario (CA)

(*) Notice: Subject to any disclaimer, the term of this patent is extended or adjusted under 35 U.S.C. 154(b) by 1057 days.

(21) Appl. No.: 12/694,561

(22) Filed: Jan. 27, 2010

(65) Prior Publication Data

US 2011/0184398 A1 Jul. 28, 2011

(51) Int. Cl.
| | | |
|---|---|---|
| *A61B 18/02* | (2006.01) | |
| *A61M 25/00* | (2006.01) | |
| *A61M 25/10* | (2013.01) | |
| *A61B 17/00* | (2006.01) | |
| *A61B 18/00* | (2006.01) | |

(52) U.S. Cl.
CPC ............ *A61B 18/02* (2013.01); *A61M 25/0069* (2013.01); *A61M 25/1011* (2013.01); *A61B 18/0218* (2013.01); *A61B 2017/003* (2013.01); *A61B 2018/0022* (2013.01); *A61B 2018/00255* (2013.01); *A61B 2018/0212* (2013.01); *A61M 2025/0079* (2013.01); *A61M 2025/1088* (2013.01); *A61M 2025/1093* (2013.01)
USPC .............................................. 606/21; 606/23

(58) Field of Classification Search
USPC ............. 606/20–23, 26; 604/103.1, 509, 917; 607/113
See application file for complete search history.

(56) References Cited

U.S. PATENT DOCUMENTS

| | | | |
|---|---|---|---|
| 5,899,898 A | | 5/1999 | Arless et al. |
| 6,235,019 B1 * | | 5/2001 | Lehmann et al. ............... 606/22 |
| 6,283,959 B1 | | 9/2001 | Lalonde et al. |
| 6,427,089 B1 * | | 7/2002 | Knowlton ..................... 607/101 |
| 2005/0209587 A1 * | | 9/2005 | Joye et al. ........................ 606/21 |
| 2007/0250050 A1 * | | 10/2007 | Lafontaine ...................... 606/21 |
| 2009/0062789 A1 * | | 3/2009 | Rioux et al. ..................... 606/41 |
| 2009/0234345 A1 * | | 9/2009 | Hon ................................ 606/21 |
| 2009/0287202 A1 | | 11/2009 | Ingle et al. |

OTHER PUBLICATIONS (PCT/CA2011/050046) PCT Notification of Transmittal of the International Search Report and the Written Opinion of the International Searching Authority, Mailed Apr. 7, 2011, 9 pages.

* cited by examiner

*Primary Examiner* — Michael Peffley
*Assistant Examiner* — Thomas Giuliani
(74) *Attorney, Agent, or Firm* — Greg A. McAllister; Stephen W. Bauer

(57) ABSTRACT

A catheter based medical device including controlled refrigerant dispersion is disclosed. The device includes a fluid injection tube that carries refrigerant from a coolant supply to the distal portion of the device. An open distal end or one or more orifices may be provided on the injection tube for the refrigerant to be expelled into an expandable chamber such as a balloon disposed on the distal portion of the catheter. The dispersion of the refrigerant from the injection tube may be controlled or manipulable to direct the refrigerant to one or more target locations.

8 Claims, 8 Drawing Sheets

CRYOBALLOON REFRIGERANT DISPERSION CONTROL

TECHNICAL FIELD

The present disclosure relates to medical devices, and in particular, to mechanisms and methods for controlling the dispersion of cryogenic fluid.

BACKGROUND

Catheter-based devices for use in surgical procedures and other medical applications are known. One category of such devices is the minimally-invasive, catheter-based device that is introduced into the vasculature. Low temperature fluid, or cryogens, may be used with such catheters to cold-treat target areas. Such devices use cold to treat selected body tissues through the energy transfer derived from thermodynamic changes occurring in the flow of a cryogen through the device. This energy transfer creates a net transfer of heat from the target tissue to the device, typically achieved by cooling a portion of the device to very low temperature through conductive and convective heat transfer between the cryogen and target tissue.

Structurally, the cryogenic fluid is injected into an expansion chamber through an orifice in an injection tube that supplies the fluid. Upon injection into the expansion chamber, the cryogen undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature cryogen through the expansion chamber acts to absorb heat from the target tissue and thereby cool the tissue to the desired temperature.

In order to cool a treatment segment at a distal end of a device having an expanded or larger surface area than the device body, for example, effective cooling may be achieved by either uniformly spraying or dispersing refrigerant onto the expanded surface of the treatment segment, or by flooding the treatment segment with a refrigerant. Flooding a treatment segment may require larger volumes of coolant, resulting in inefficient use and increased costs. When flooding a treatment segment, the phase change of the cryogen is not controlled and may not occur at the location where the catheter contacts the tissue which is intended to be ablated. As well, the cryogen may return from the balloon as a cold liquid that will cool the catheter shaft, potentially ablating adjacent tissue unintentionally. These shortcomings make the substantially uniform spraying or dispersion of coolant an attractive alternative. Devices as depicted in U.S. Pat. No. 6,235,019 provide multiple coolant injection tubes. Alternatively, as shown in U.S. Pat. No. 5,899,898, a single injection tube can be provided with openings along its length.

However, the dispersion of coolant from these devices is performed in a fixed direction, i.e., the orifice or ports from which the coolant is sprayed disperse the coolant in a non-varying direction. It is therefore desirable to provide a device which optimizes the cooling power of the flow of cryogenic fluid therethrough, namely through controllably directing a supply of high pressure cryogen to a target tissue and thereby increase the cooling efficiency.

SUMMARY

Various embodiments of the present disclosure provide for catheter based medical devices having mechanisms for controlling or manipulating the dispersion of coolant to a particular location.

In one embodiment, a catheter having a fluid injection tube is disclosed. The fluid injection tube includes a proximal and a distal end, with a distal portion of the fluid injection tube includes one or more orifices or an open absolute distal end. A dispersion control element may be coupled to the fluid injection tube. The dispersion control element may be mechanically, electrically or magnetically controlled to manipulate the angle of dispersion of fluid from the fluid injection tube.

In another embodiment, a fluid injection tube having a proximal and distal end may be included in a catheter with a distal portion of the fluid injection tube comprising a magnetic material. The catheter may additionally include selectively magnetizable components on an expandable balloon of the catheter such that one of the magnetizable components is activated to attract the magnetic segment of the fluid injection tube. The magnetized component causes the injection tube to be oriented in a particular direction thus causing the fluid to be dispersed at a particular angle.

In another embodiment, a catheter is provided having a sensing element disposed on the outer perimeter of an exterior balloon. The sensing element determines a location of contact between the catheter and a patient's tissue. A distal opening or orifice of a fluid injection tube included in the catheter may be oriented such that dispersion of fluid from the injection tube is directed at the point of contact with the patient's tissue.

In another embodiment, the present disclosure provides a medical device for thermally affecting tissue including a steering element. A fluid injection tube having a proximal end and a bifurcated distal end may be provided such that the bifurcated distal end is in contact with the steering element. The injection tube may be moved longitudinally and in contact with the steering element such that the angle of the bifurcated distal end changes thereby changing the direction of dispersion of fluid from the injection tube.

In another embodiment, a catheter may include an injection tube having a flexible steering element disposed at a distal end of the injection tube. A proximal end of the steering element may be anchored to an outer tube of the catheter while permitting the structure of the steering element to flex in response to a mechanical force applied by the injection tube. A plurality of ports may be disposed on the distal end of the steering element, with the angle of the ports being changeable with the application of mechanical force on the injection tube.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

The following description is exemplary in nature and is not intended to limit the scope, applicability, or configuration of the present disclosure in any way. Rather, the description provides practical illustrations for implementing exemplary embodiments of the present disclosure.

Figure 1:
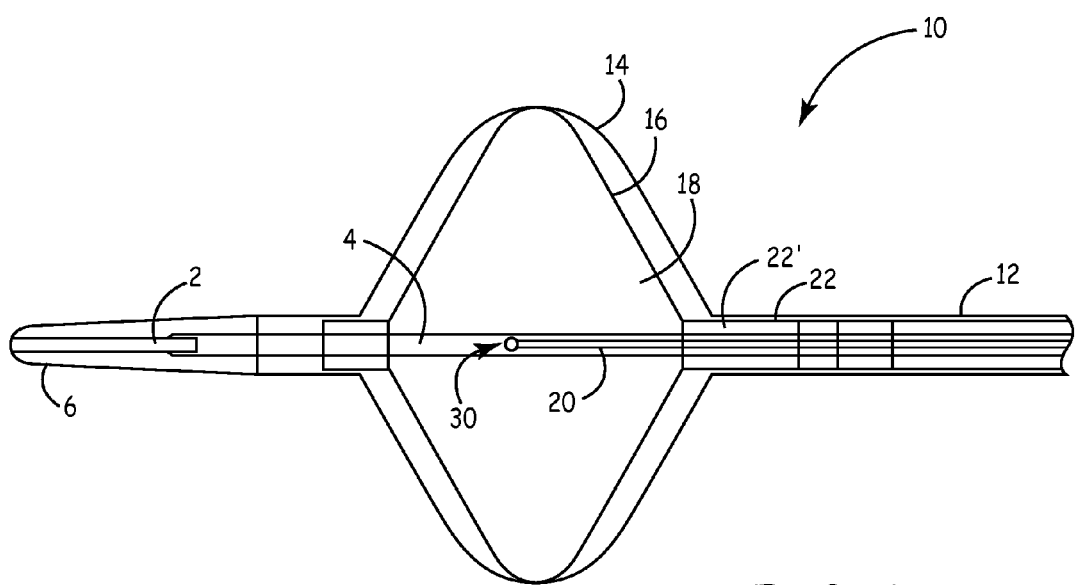
FIG. 1 shows a longitudinal cross-sectional view of a catheter based medical device, of an exemplary embodiment of the present disclosure.

FIG. 1 shows a longitudinal cross-sectional view of a catheter 10, an exemplary embodiment of the present disclosure. Catheter 10 comprises an outer tube 12 which may be coupled to an outer balloon 14 at the distal portion of catheter 10. An inner balloon 16 may be disposed within the outer balloon 14. The void within inner balloon 16 defines an expansion chamber 18. In use, both the outer balloon 14 and inner balloon 16 may be expanded concurrently to contact a blood vessel, or chamber during an ablation procedure.

Although the exemplary embodiment depicts a gap between portions of the outer balloon 14 and inner balloon 16, it should be noted that the entire perimeter of both outer balloon 14 and inner balloon 16 will typically be in contact. The outer balloon 14 contains leaks in the inner balloon 16 should they occur. Low pressure or vacuum return lumens 22 and 22' may be in fluid communication with the interior of the first and second balloons, respectively.

Outer tube 12 of the catheter 10 defines a lumen that may circumferentially enclose an injection tube 20 so that the tubes may be substantially coaxially disposed with respect to each other, such that a longitudinal centerline (not shown) of outer tuber 12 approximately coincides with the longitudinal centerline (not shown) of injection tube 20. Injection tube 20 may substantially span the length of outer tube 12 and may terminate at a point slightly more distal to the absolute distal end of outer tube 12 such as within the second balloon 16.

Injection tube 20 may be disposed over a guidewire structure 4 such as a tube, a wire or a shim that passes through or is contained within the lumen defined by outer tube 12. The guidewire structure 4 may include part of a catheter steering element, such as a tube 2 that defines a passage for a guide wire (not shown). As shown, the tube 2 has an open proximal end that is substantially coterminous with the proximal end of the catheter and may also include an open distal end that is substantially coterminous with the distal end of the catheter. The guide wire is suitable for placement into the vasculature of a patient and the tube 2 slides over the wire (i.e., the wire goes through the passage), for guiding the distal portion of the catheter 10 to a desired location using techniques known in the art. The distal end of the catheter 10 can include a soft tip element 6 to minimize or prevent tissue trauma.

A dispersion control element 30 may be coupled to the distal portion of injection tube 20. The dispersion control element 30 provides an exit point for the cryogen flowing through the injection tube 20 into the expansion chamber 18. The direction of dispersion of refrigerant within the expansion chamber defined by first outer balloon 14 and second balloon 16 is generally directed by the angle at which the fluid, such as a cryogenic fluid, is dispersed from the injection tube 20. Conventional injection tubes generally have one or more orifices from which the refrigerant is sprayed. However, the location at which the refrigerant contacts inner balloon 16 as it is sprayed from the orifice will vary depending on the orientation of the injection tube 20, the size to which the balloons have been expanded and even the orientation of the orifice.

High pressure, low temperature cryogen is supplied to the catheter 10, and initially enters the catheter 10 as it flows through the injection tube 20 towards the expansion chamber 18. Cryogenic fluid, upon flowing through the injection tube 20, exits the injection tube 20 through the dispersion control element 30, and flows into the expansion chamber 18. After flowing into the expansion chamber 18, cryogen is induced through a negative pressure gradient to flow back towards the proximate portion of the catheter 10 through the return lumen 22' defined by the interior surface of the outer tube 12.

Dispersion control element 30 is adjustable to control the angle of dispersion and hence the location of contact of the fluid. The adjustment to the dispersion control element 30 may be mechanical (such as described in more detail in relation to FIGS. 3A and 3B), electrical, or through any other suitable means. Adjustment of the angle of dispersion from dispersion control element 30 directs the fluid to a desired location on the second balloon 16 and first outer balloon 14. As such, in ablation procedures, adjustment of the angle of dispersion of fluid from dispersion control element 30 adjusts the angle of fluid spray to target the ablation zone. It is emphasized that the illustrative coupling location of dispersion control element 30 is but one particular arrangement, and that the dispersion control element 30 may be coupled to the injection tube 20 at any desired location.

All of tubes 2, 4, 12, and 20 are preferably made of a flexible solid material, such as polyimide, or other polymer, metal, or combination thereof, including those suitable for the transport of high pressure fluids, as is well known to those skilled in the art. A portion of injection tube 20 may be coupled to guidewire structure 4 through adhesion. It is understood that any number of adhesion or coupling mechanisms or devices may be used for the coupling, preferably including, but not limited to a glue, epoxy, or other suitable coupling agent, as is well known to those skilled in the art.

The first outer balloon 14 and second outer balloon 16 may be made of a thermally-transmissive material, such as those described in U.S. Pat. No. 6,575,933 issued to Dan Wittenberger et. al, incorporated herein by reference in its entirety. Although many materials and structures may be thermally conductive or thermally transmissive if cooled to a very low temperature, as used herein, a "thermally-transmissive" element is intended to broadly encompass any element that readily conducts heat.

Figure 2A:
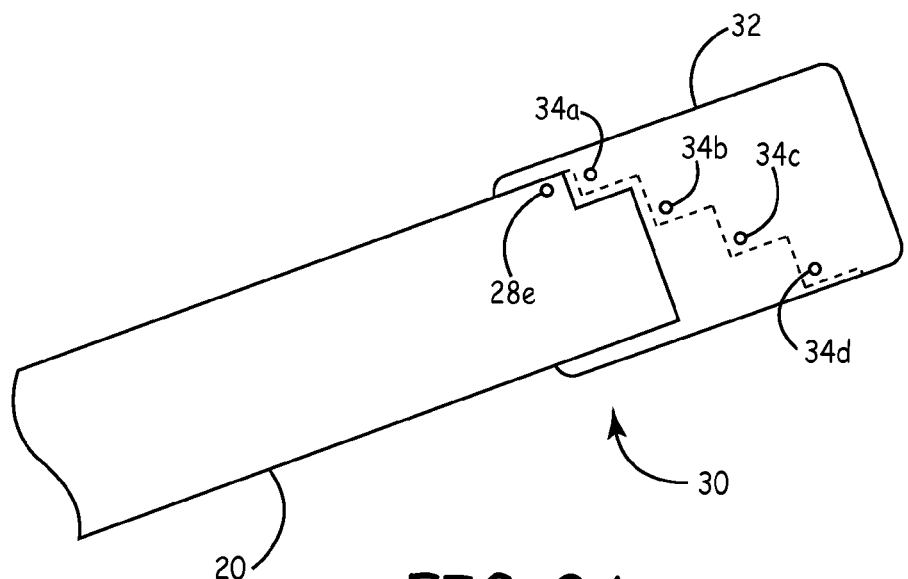
FIG. 2A illustrates a cross-sectional view of an exemplary embodiment of the dispersion control element for a catheter based medical device constructed in accordance with the principles of the present disclosure.

FIG. 2A illustrates a cross-sectional view of an exemplary embodiment of the dispersion control element 30 of FIG. 1. The dispersion control element 30 may be mechanically controlled to adjust the flow angle of fluid flowing in the injection tube 20. Dispersion control element 30 includes a nozzle 32 or other flow regulating device that is coupled to the absolute distal end of injection tube 20. Nozzle 32 includes a plurality of orifices 34a, 34b, 34c, and 34d which have varying angles.

The injection tube 20 includes an orifice 28 through which fluid flowing through the injection tube exits. One of the orifices 34a, 34b, 34c, and 34d on nozzle 32 may be aligned with orifice 28e on injection tube 20 to direct the fluid dispersion in the desired direction. Dispersion control element 30 may be disposed over injection tube 20. In an exemplary embodiment, the dispersion control element 30 may be arranged in a manner that may permit rotational engagement such as through the use of a threaded coupling.

Figure 2B:
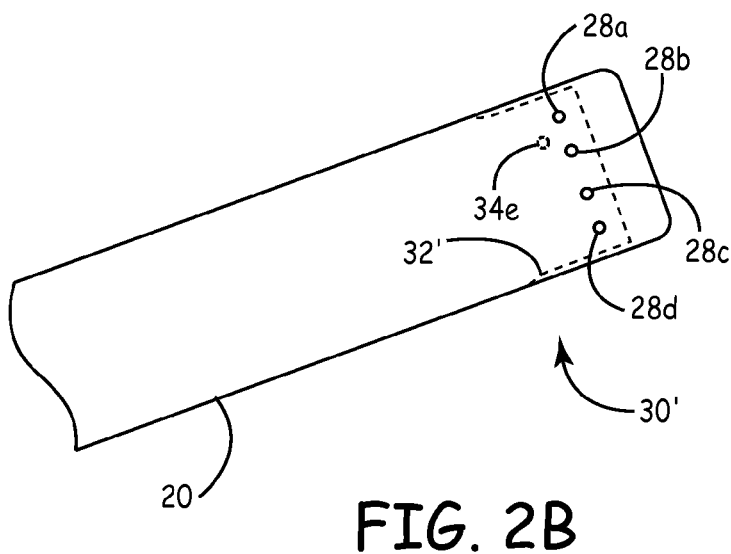
FIG. 2B illustrates a cross-sectional view of an alternative exemplary embodiment of a dispersion control element for a catheter based medical device constructed in accordance with the principles of the present disclosure.

FIG. 2B illustrates a cross-sectional view of an alternative exemplary embodiment of a dispersion control element 30'. The dispersion control element 30' includes a nozzle 32' that is disposed within the injection tube 20. Nozzle 32' includes an orifice 34e through which fluid flowing through injection tube 20 exits. The fluid, after exiting through orifice 34e, flows through one of the orifices 28a, 28b, 28c, and 28d disposed on the exterior of injection tube 20. Dispersion control element 30' may suitably be electrically coupled to a control device (not shown) to adjust the location of orifice 34e with respect to the orifices 28a, 28b, 28c, and 28d on the injection tube 20.

Figure 3:
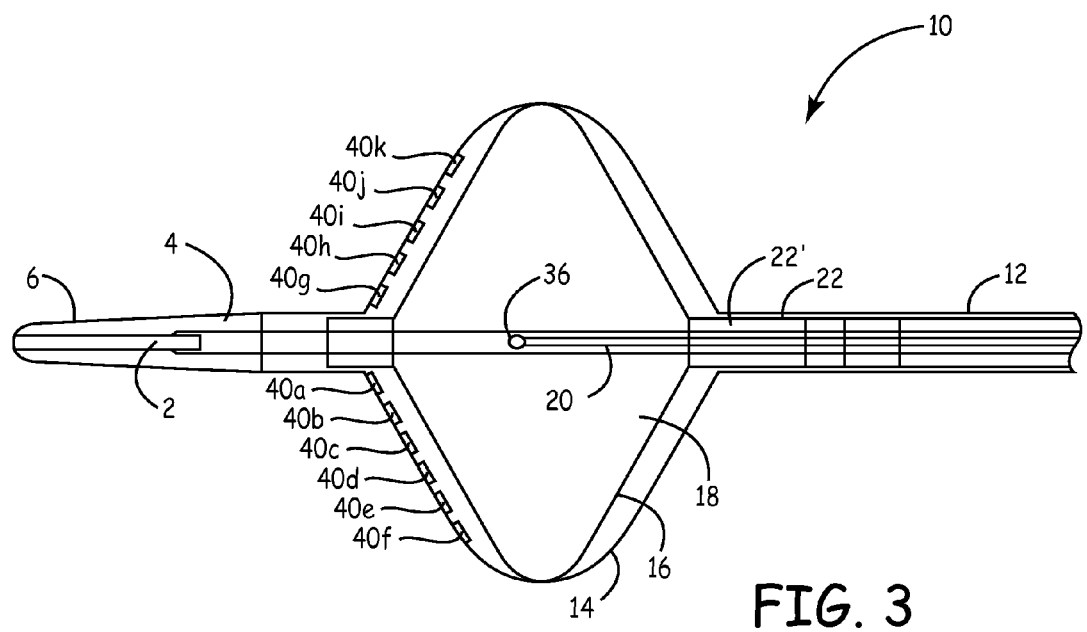
FIG. 3 illustrates a side cross-sectional view of an alternative embodiment of a catheter based medical device constructed in accordance with the principles of the present disclosure.

Referring now to FIG. 3, a longitudinal cross-sectional view of an alternative embodiment of catheter 10 is illustrated. The injection tube 20 on catheter 10 may be open at the absolute distal end. Alternatively, or additionally, one or more orifices (not shown) may be disposed along the sidewall of injection tube 20. Fluid contained within or flowing through the injection tube 20 may be dispersed at the open absolute distal end or the one or more orifices on the injection tube 20 sidewall or both A plurality of magnetizable components 40a-k are coupled to the inner wall of first outer balloon 14. Each of the magnetizable components 40a-k of the exemplary embodiment may be a discrete component that can be separately energized to create a magnetic flux. The magnetizable components 40a-k may be electrically coupled to a conductor (not shown) that connects the magnetizable components 40a-k to a controller (not shown) that may be operated by a user to selectively activate one of the magnetizable components 40a-k. The selective activation of one of the magnetizable components 40a-k causes the selected component to generate a magnetic field for attraction of another magnetic component. The arrangement of the magnetizable components 40a-k may include a gap that provides separation between each of the components to effectively isolate the magnetic field in a single location. However, alternative embodiments may simply include a single magnetic plate that may include discrete regions that can be selectively energized to generate discrete magnetic field at various locations.

A magnetic member 36 may be disposed at the distal end of injection tube 20. The magnetic member 36 may be a discrete element coupled on injection tube 20. Alternatively, magnetic member 36 may be integrated into the injection tube 20. The magnetic properties of magnetic member 36 may be such that the selective activation of any of the magnetic components 40a-k would result in a magnetic attraction of magnetic member 36. As a result of the magnetic attraction of magnetic member 36, the injection tube 20 may be deflected in a desired direction and the open end or one or more orifices angled to direct the dispersion of fluid at the targeted location.

Figure 4:
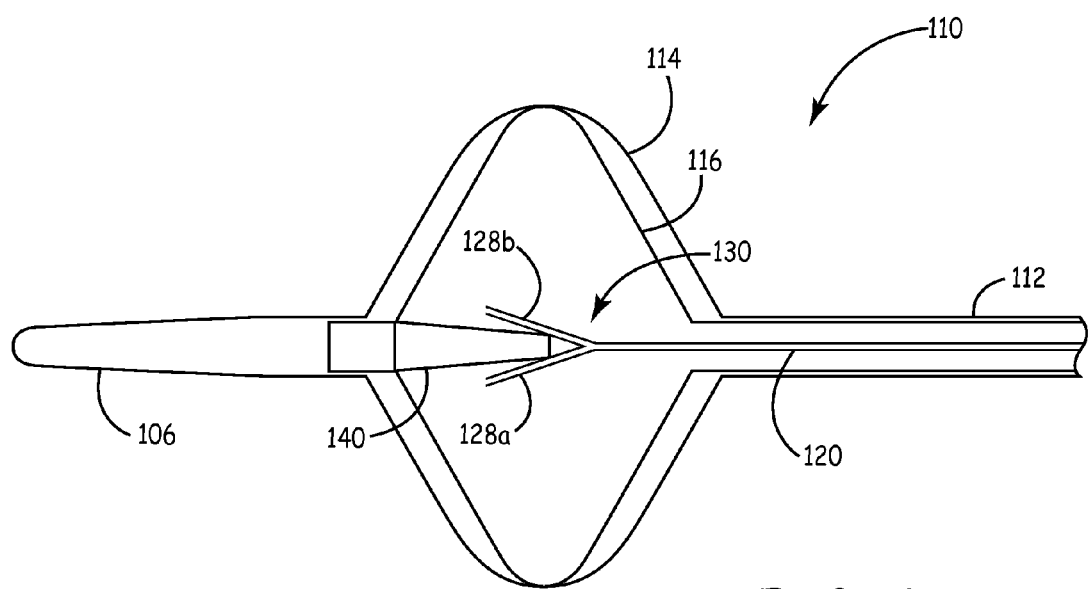
FIG. 4 shows a cross-sectional view of an alternative embodiment of a catheter based medical device constructed in accordance with the principles of the present disclosure.

Turning to FIG. 4, an alternative illustration of a catheter 110 is illustrated. The exemplary embodiment illustrates catheter 110 having an outer tube 112 defining a lumen through which an injection tube 120 is disposed. A first outer balloon 114 is coupled to outer tube 112. First outer balloon 114 encapsulates a second balloon 116 and the first and second balloons 114, 116 define an expandable chamber. A soft tip element 106 is coupled to the distal end of outer tube 112.

Injection tube 120 may terminate within the expandable chamber. Injection tube 120 may be bifurcated or branched at its distal end 130 with bifurcated distal ends 128a, 128b. The bifurcated ends 128a, 128b may be open to permit fluid to be expelled and directed at a target location on second balloon 116. Bifurcated ends 128a, 128b are preferably constructed from a flexible material. The injection tube may also terminate in branched ends that have multiple branches distributed about the central axis of distal end 130 of injection tube 120.

A steering element 140 may be disposed within the expandable chamber and may be coupled to the second balloon 116. Steering element 140 may be constructed from a rigid material such as stainless steel and have a tapered proximal end that is in contact with bifurcated distal ends 128a, 128b. The injection tube 120 may be moveable within the expandable chamber and lumen of outer tube 112 in a longitudinal and rotational direction. As such, longitudinal movement of the injection tube 120 will cause the angle between bifurcated ends 128a, 128b to increase or decrease. An increase or decrease in the angle between bifurcated ends 128a, 128b will result in a corresponding change to the point of contact of the fluid expelled from the openings in the bifurcated ends 128a, 128b.

Figure 5:
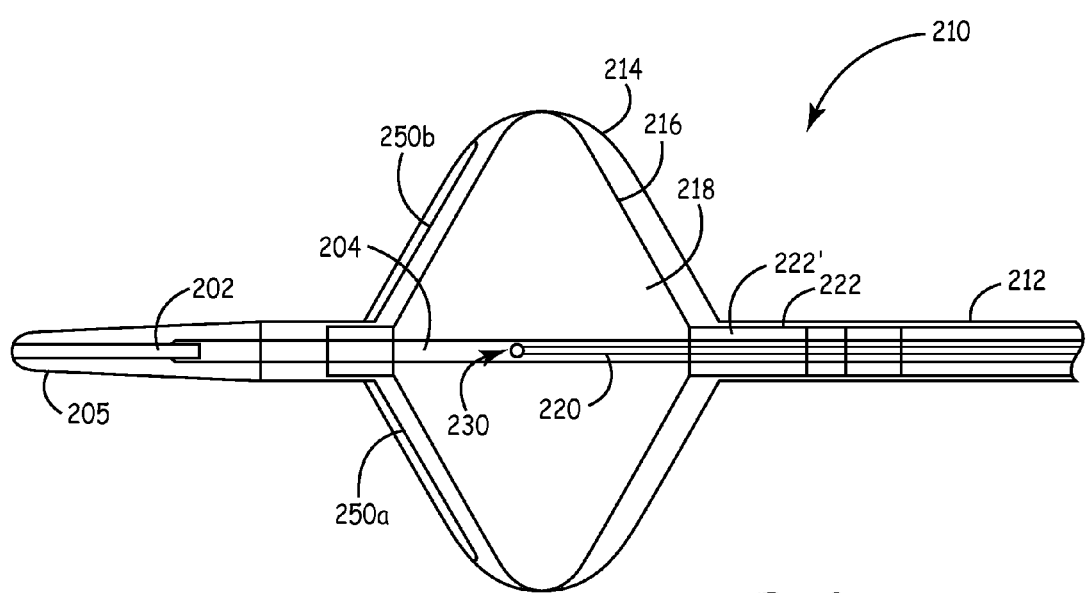
FIG. 5 depicts a cross-sectional view of an alternative embodiment of a catheter based medical device constructed in accordance with the principles of the present disclosure.

FIG. 5 shows an alternative embodiment of a catheter 210 in accordance with principles of the present disclosure. Catheter 210 includes an outer tube 212 that defines a lumen. Catheter 210 further includes a first outer balloon 214 that encapsulates a second balloon 216 and the dual balloon structure defines an expandable chamber 218. The distal end of the outer tube 212 may include a soft tip element 206. A structure 204 such as a tube may be disposed within the lumen of the outer tube 212. Structure 204 may have an open proximal end that is substantially coterminous with the proximal end of outer tube 212 and an open distal end that is substantially coterminous with the distal end of the outer tube 212. The structure 204 may define a passage for insertion of a guidewire that is suitable for placement into the vasculature of a patient and over which the catheter 210 slides. Low pressure or vacuum return lumens 222 and 222' are in fluid communication with the interior of the first and second balloons, respectively.

An injection tube 220 may be disposed within the lumen of outer tube 212 with the injection tube 220 terminating within the expandable chamber 218. A portion of the injection tube 220 may be coupled to the structure 204. The distal end of injection tube 220 may include an orifice at the absolute distal end or along the side wall. Injection tube 220 may also include a dispersion control element 230 that may be similar to the dispersion control element 30 described with reference to FIG. 1. Alternatively, or in addition, the distal portion of injection tube 220 may comprise a magnetic material as described in relation to FIG. 3. In any event, construction of injection tube 220 permits control of the angle of dispersion of fluid expelled from the injection tube 220 through, for example, the mechanisms disclosed in relation to the aforementioned above figures.

Catheter 210 also includes a sensing mechanism for determining the location of contact between the first outer balloon 214 and a patient's tissue during operation. Sensing elements 250a, 250b may be disposed on the inner surface of outer balloon 214 to monitor and locate the point of contact with the patient's tissue. The sensing elements 250a, 250b may comprise force sensors such as a strain gauge. The sensing elements 250a, 250b may measure the force exerted on the circumference of the outer balloon 214 and provide an indication of the point of contact.

The orientation of the distal portion of injection tube 220 may be coordinated with the point of contact of the outer balloon 214 based on the signal sensed by sensing elements 250a, 250b. The signals generated by sensing elements 250a, 250b may be transmitted to a control module (not shown) that may coordinate motion of the injection tube 220 to change the angle at which fluid is expelled from the distal opening or orifice. The contact signals generated by sensing elements 250a, 250b may additionally be employed in a feedback based loop to cause the angle to be adjusted at any time during operation of the catheter 210.

Alternatively, contact between the outer tube 214 and the vasculature may result in generation of a magnetic field that would cause a deflection in the injection tube and hence a change in the angle of dispersion of fluid from the distal opening or orifices.

Figure 6:
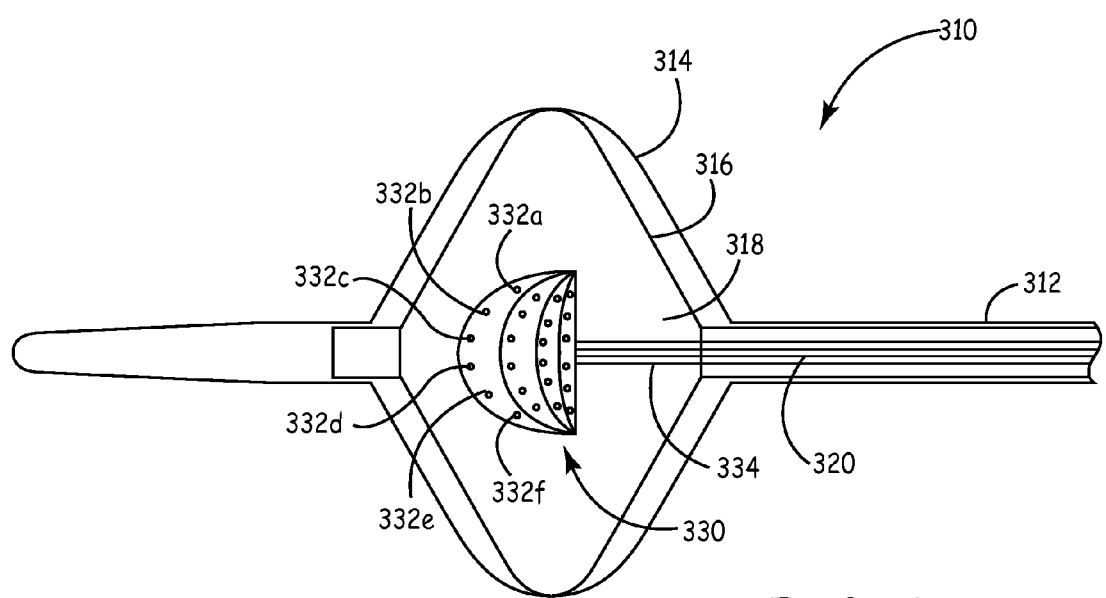
FIG. 6 illustrates a cross-sectional view of an alternative embodiment of a catheter based medical device constructed in accordance with the principles of the present disclosure.

Referring now to FIG. 6, an alternative embodiment of a catheter 310 constructed in accordance with embodiments of the present disclosure is shown. The catheter 310 may include an outer tube 312 that defines a lumen through which an injection tube 320 is disposed. Outer tube 312 may also be coupled to a first outer balloon 314 and a second balloon 316. The dual balloon structure may define an expandable chamber 318. An injection tube 320 may be disposed within the lumen of outer tube 312 and injection tube 320 may terminate within the expandable chamber 318.

The distal portion of injection tube 320 may be coupled to a fluid dispersion element 330 to disperse fluid expelled from a distal opening of the injection tube 320. The dispersion element 330 may have a plurality of orifices 332a, 332b, 332c, 332d, 332e and 332f. Dispersion element 330 may be coupled at its proximal end to outer tube 312 through an anchor 334. The injection tube 320 may be moveable and slidable about the dispersion element 330. The dispersion element 330 may be constructed from a flexible material such that injection tube 320 may be pushed longitudinally to cause the shape of the dispersion element 330 to change thereby changing the angle of dispersion of fluid expelled from the injection tube 320.

As such, fluid may egress from the orifices 332a, 332b, 332c, 332d, 332e and 332f with the dispersion element 330 being adjusted accordingly to provide for varying angles of spray distribution.

Figure 7:
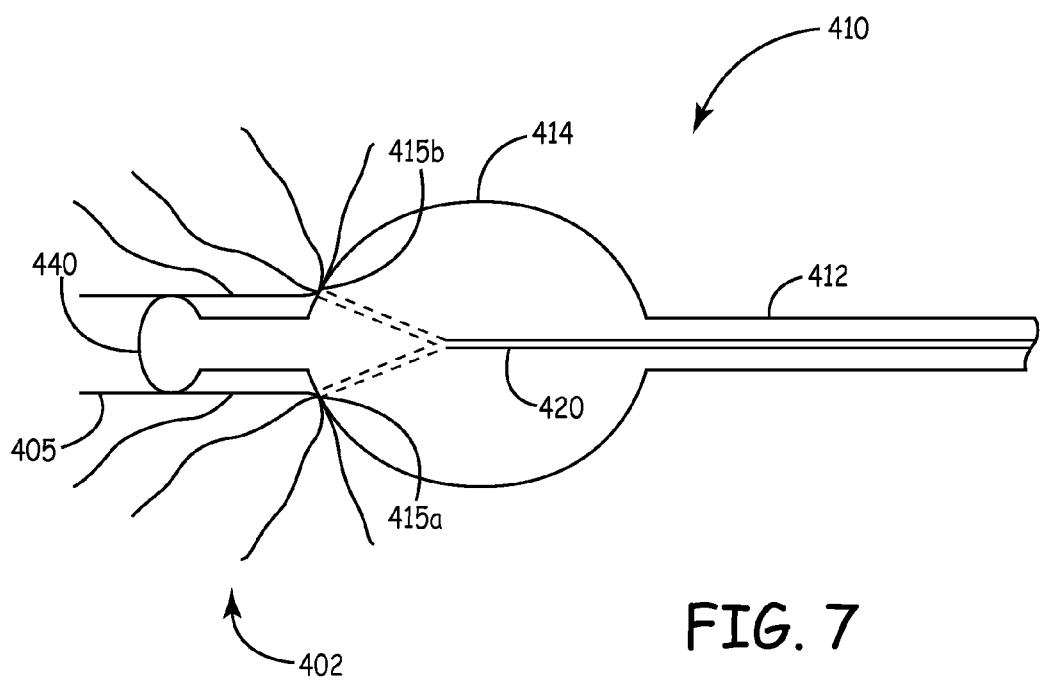
FIG. 7 shows a cross-sectional view of an alternative embodiment of a catheter based medical device as contemplated in one implementation in accordance with the principles of the present disclosure.

Turning now to FIG. 7, an alternative embodiment of a catheter 410 of the present disclosure is shown in use. The catheter 410 is illustrated abutting a vein 405 of a patient 402. Specifically, region 415a and 415b of proximal balloon 414 are shown abutting the opening of vein 405 as would be the case during an ablation procedure. Proximal balloon 414 is coupled to a distal portion of outer tube 412. Outer tube 412 also defines a lumen through which an injection tube 420 is disposed. A distal balloon 440 is coupled to the absolute distal end of the outer tube 412. The distal balloon 440 is expanded to anchor the catheter 410 inside the lumen of vein 405.

The angle of the distal portion of injection tube 420 may be changed in correlation to the expansion of the distal balloon 440. The change in the angle of distal portion may be achieved through any of the above described methods or any other electrical, mechanical or magnetic methods. As such, the dispersion of fluid from the distal opening or orifice of injection tube 420 may be varied depending on the size of the vein based upon the inflation of the distal balloon 440.

Figure 8A:
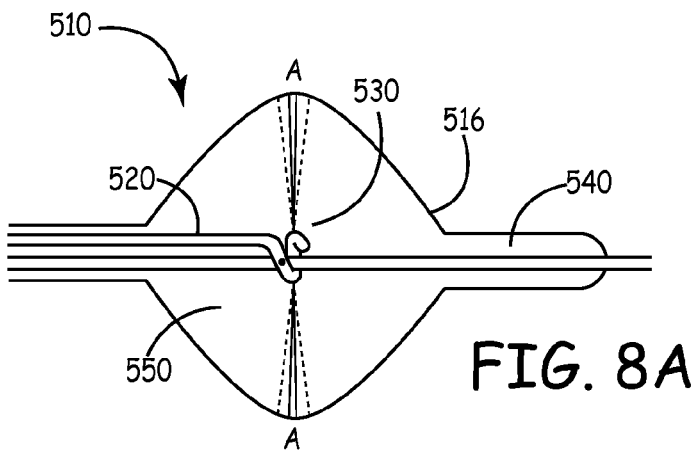
FIGS. 8A-8D show cross-sectional views of an alternative embodiment of a catheter based medical device as contemplated in one implementation in accordance with the principles of the present disclosure.
Figure 8B:
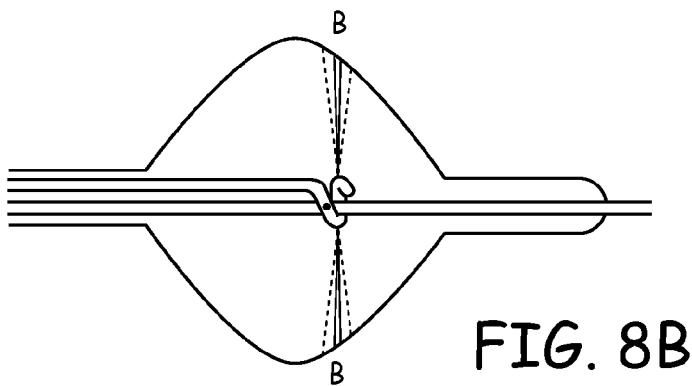
Figure 8C:
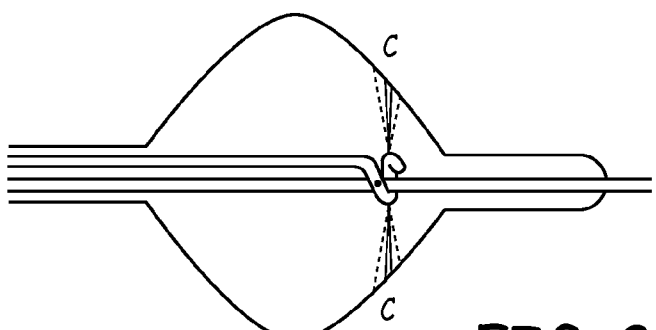
Figure 8D:
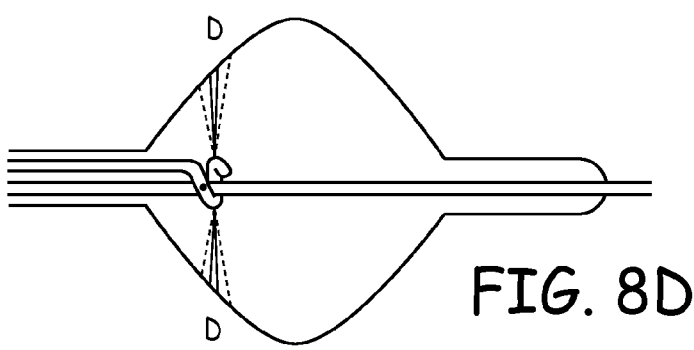

FIGS. 8A-8D illustrate a cross-sectional view of an alternative exemplary embodiment of catheter 510. In this embodiment, dispersion control element 530 is slidably disposed over guidewire 540 such as by partially or completely encircling guidewire 540. Injection tube 520 may be advanced or retracted by any suitable mechanism (not shown) to position dispersal control element 530 relative to inner balloon 516. In FIG. 8A, the injection tube 520 has been positioned such that cryogen 550 is sprayed along chord A-A of inner balloon 516. Inner balloon 516 would typically be enclosed within an outer balloon (not shown) as disclosed in previous embodiments. In FIG. 8B, injection tube 520 has been positioned such that cryogen 550 is sprayed along chord B-B of inner balloon 516. In FIG. 8C, injection tube 520 has been positioned such that cryogen 550 is sprayed along chord C-C of inner balloon 516. In FIG. 8D, injection tube 520 has been positioned such that cryogen 550 is sprayed along chord D-D of inner balloon 516. Selecting the chord on inner balloon that receives the spray of cryogen 550 facilitates different uses for the device in performing ablation treatments. Spraying the cryogen 550 on the distal portion of balloon 516 facilitates procedures in which the balloon is placed in the heart through the superior or inferior vena cava, while spraying the cryogen 550 on the proximal portion of the balloon, such as chord D-D, facilitates procedures in which the balloon is placed in the heart in a retrograde manner, such as through the pulmonary veins.

It should be noted that although the embodiments of the present disclosure have generally been described in the context of a single injection tube, this is merely for simplicity and ease of discussion. Alternative embodiments could employ a plurality of injection tubes and of course the orientation of fluid dispersion from each of the plurality of injection tubes could be independently adjusted. In other alternative embodiments, the expandable chamber defined by the dual balloon structure can also be a substantially uniform diameter passage within a wall portion of the catheter, one lumen of a multi-lumen configuration, or central lumen within a catheter that is coaxial with the longitudinal axis of the catheter.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   an outer tube defining a lumen;
   an injection tube disposed within the lumen having a proximal end and a distal end, wherein the distal end is bifurcated having a first end and a second end;
   at least one orifice disposed on each of the first and second ends;
   a steering element coupled to the outer tube and in contact with the first end and the second end, wherein longitudinal movement of the injection tube relative to the steering element controls an angle between the first and second ends to vary an angle of dispersion from the at least one orifice disposed on each of the first and second ends.

2. The medical device of claim 1, wherein the steering element is movable within the lumen to change an orientation of the at least one orifice disposed on each of the first and second ends.

3. The medical device of claim 1, wherein the steering element is coupled to a fixed location and each of the first and second ends are moveable within the lumen to change an orientation of the at least one orifice disposed on each of the first and second ends.

4. The medical device of claim 1, wherein the first and second ends are moveable within the outer tube to change an orientation of the at least one orifice disposed on each of the first and second ends.

5. The medical device of claim 1, wherein the injection tube spans the length of the outer tube.

6. The medical device of claim 1, further comprising at least one balloon coupled to the outer tube.

7. The medical device of claim 6, further comprising a sensing element disposed on the balloon, said sensing element configured to output a signal that is indicative of a region of contact of the balloon with a patient.

8. The medical device of claim 7, wherein said signal is indicative of a force exerted on the balloon.

* * * * *